(12) United States Patent
Alageel et al.

(10) Patent No.: US 10,918,719 B2
(45) Date of Patent: Feb. 16, 2021

(54) METHODS FOR CROSS-LINKING CORNEAL COLLAGEN WITH VERTEPORFIN FOR THE TREATMENT OF DISORDERS OF THE EYE

(71) Applicant: Massachusetts Eye and Ear Infirmary, Boston, MA (US)

(72) Inventors: Saleh Alageel, Boston, MA (US); Joseph B. Ciolino, Boston, MA (US)

(73) Assignee: Massachusetts Eye and Ear Infirmary, Boston, MA (US)

( * ) Notice: Subject to any disclaimer, the term of this patent is extended or adjusted under 35 U.S.C. 154(b) by 0 days.

(21) Appl. No.: 15/121,909

(22) PCT Filed: Feb. 26, 2015

(86) PCT No.: PCT/US2015/017776
§ 371 (c)(1),
(2) Date: Aug. 26, 2016

(87) PCT Pub. No.: WO2015/130944
PCT Pub. Date: Sep. 3, 2015

(65) Prior Publication Data
US 2017/0043015 A1 Feb. 16, 2017

Related U.S. Application Data

(60) Provisional application No. 61/946,310, filed on Feb. 28, 2014.

(51) Int. Cl.
*A61K 41/00* (2020.01)
*A61K 31/409* (2006.01)
(Continued)

(52) U.S. Cl.
CPC ........ *A61K 41/0071* (2013.01); *A61F 9/0008* (2013.01); *A61F 9/008* (2013.01);
(Continued)

(58) Field of Classification Search
None
See application file for complete search history.

(56) References Cited

U.S. PATENT DOCUMENTS 7,073,510 B2 * 7/2006 Redmond ............... A61F 9/008
128/898
7,282,215 B2 * 10/2007 Chowdhary ....... A61K 41/0057
424/450
(Continued)

OTHER PUBLICATIONS

Visudyne—verteporfin for injection injection, powder, lyophilized, for solution, Apr. 7, 2010, https://dailymed.nlm.nih.gov/dailymed/drugInfo.cfm?setid=31512723-9ff0-4e18-aa3a-55ab833038c6; retrieved Feb. 26, 2018.*

(Continued)

*Primary Examiner* — Christopher Koharski
*Assistant Examiner* — James Moss
(74) *Attorney, Agent, or Firm* — Fish & Richardson P.C.

(57) ABSTRACT

Described are compositions and methods of using verteporfin-based photodynamic therapy (PDT) to increase the biomechanical strength of the cornea. More particularly, described herein are compositions and methods for cross-linking collagen in corneal tissue which are useful in the treatment of corneal ectatic disorders.

10 Claims, 7 Drawing Sheets

(51) Int. Cl.

| | |
|---|---|
| A61N 5/06 | (2006.01) |
| A61F 9/008 | (2006.01) |
| A61K 47/36 | (2006.01) |
| A61F 9/00 | (2006.01) |
| A61K 9/00 | (2006.01) |
| A61K 9/08 | (2006.01) |
| A61N 5/067 | (2006.01) |

(52) U.S. Cl.
CPC ............. *A61K 9/0048* (2013.01); *A61K 9/08* (2013.01); *A61K 31/409* (2013.01); *A61K 47/36* (2013.01); *A61N 5/062* (2013.01); *A61F 9/00804* (2013.01); *A61F 2009/00853* (2013.01); *A61F 2009/00872* (2013.01); *A61N 2005/067* (2013.01)

(56) References Cited

U.S. PATENT DOCUMENTS

| | | | | |
|---|---|---|---|---|
| 7,419,666 | B1* | 9/2008 | Iliaki | A61K 39/39541 424/144.1 |
| 2002/0103180 | A1* | 8/2002 | Richter | A61P 31/00 514/185 |
| 2006/0052286 | A1* | 3/2006 | Garen | A61K 38/41 514/2.4 |
| 2006/0204504 | A1* | 9/2006 | Gragoudas | A61K 31/353 424/155.1 |
| 2006/0223750 | A1* | 10/2006 | Burke | A61K 47/61 514/418 |
| 2011/0282333 | A1* | 11/2011 | Herekar | A61F 9/00821 606/5 |
| 2012/0310141 | A1* | 12/2012 | Kornfield | A61F 9/008 604/20 |
| 2013/0060187 | A1* | 3/2013 | Friedman | A61F 9/0008 604/20 |

OTHER PUBLICATIONS

Pavel Kamaev, Marc D. Friedman, Evan Sherr, David Muller; Photochemical Kinetics of Corneal Cross-Linking with Riboflavin; Apr. 2012; Investigative Opthamalogy & Visual Science, Apr. 2012, vol. 53, 2360-2367.*

"Lesion." Merriam-Webster.com. https://www.merriam-webster.com/dictionary/lesion (Sep. 24, 2018).*

"Wound." Merriam-Webster.com. https://www.merriam-webster.com/dictionary/wound (Sep. 24, 2018).*

John Kanellopoulos, "Preventing Ectasia With Cross-linking After PRK or LASIK", Cataract & Refractive Surgery Today, May 2012, https://crstoday.com/wp-content/themes/crst/assets/downloads/crst0512_mf6_kanell.pdf, viewed on Feb. 25, 2019.*

Kyung-Chu Yoon et al., Photodynamic Therapy with Verteporfin for Corneal Neovascularization, American Journal of Ophthalmology, vol. 144, Issue 3, Sep. 2007, pp. 390-395, https://doi.org/10.1016/j.ajo.2007.05.028, viewed on Mar. 26, 2019.*

A. J. Kanellopoulos (2012). "Long-term safety and efficacy follow-up of prophylactic higher fluence collagen cross-linking in high myopic laser-assisted in situ keratomileusis". Clinical ophthalmology (Auckland, N .Z.), 6, 1125-1130. https://doi.org/10.2147/OPTH.S31256, viewed on Mar. 26, 2019.*

Michelacci, Yara M. "Collagens and proteoglycans of the corneal extracellular matrix." Brazilian journal of medical and biological research=Revista brasileira de pesquisas medicas e biologicas 36 8 (2003): 1037-4., viewed on Mar. 26, 2019.*

Homer Chiang et al., Treatment of Corneal Neovascularization, EyeNet Magazine, Opthalmic Pearls, pp. 35-36. Oct. 2013, https://www.aao.org/eyenet/article/treatnnent-of-corneal-neovascularization, viewed on Mar. 26, 2020.*

Ahmed et al., "Comparative study of corneal strip extensometry and inflation tests," JR Soc Interface, 22; 2(3): 177-185, 2005.

Al-Abdullah et al., "Resolution of bilateral corneal neovascularization and lipid keratopathy after photodynamic therapy with verteporfin," Optometry, 2011, 82(4):212-4.

Al-Torbak et al., "Photodynamic therapy with verteporfin for corneal neovascularization," Middle East Afr J Ophthalmol, 19(2):185-9, 2012.

Brooks et al., "Photodynamic therapy for corneal neovascularization and lipid degeneration." Br J Ophthalmol 88:840, 2004.

Celik et al., "Accelerated corneal crosslinking concurrent with laser in situ keratomileusis," J. Cataract Refract. Surg, 2012, 38(8): 1424-1431.

Chai et al., "Quantitative assessment of UVA-riboflavin corneal cross-linking using nonlinear optical microscopy," Invest. Ophthalmol Visual Sci. 52(7), 4231-4238, 2011.

Charulatha and Rajaram, "Crosslinking density and resorption of dimethyl 30 suberimidate-treated collagen," J Biomed Mater Res, 1997, 36: 478-486.

Comaish et al., "Laser in situ keratomileusis for residual myopia after photorefractive keratectomy," Journal of Cataract & Refractive Surgery, May 2002, 28: 775-781.

Condon et al., "Long-term results of laser in situ keratomileusis for high myopia: risk for ectasia," J. Cataract Refract. Surg, 2007, 33(4): 583-590.

Fossarello et al., "Photodynamic therapy of corneal neovascularization with verteporfin," Cornea, 2003, 22:485-8.

Hafezi et al., "Collagen crosslinking with ultraviolet-A and hypoosmolar riboflavin solution in thin corneas," J. Cataract Refract. Surg. 35(4), 621-624, 2009.

Igarashi et al., Topographical alteration in the cornea after photodynamic therapy for neovascularization in lipid keratopathy, Jpn J Opthalmol, , 2009, 53: 648-668.

International Preliminary Report on Patentability in International Application No. PCT/US2015/017776, dated Sep. 15, 2016, 6 pages.

International Search Report and Written Opinion in International Application No. PCT/US2015/017776, dated May 7, 2015, 8 pages.

Jenkins et al., "Intra-arterial photodynamic therapy using 5-ALA in a swine model," Eur J Vasc Endovasc Surg, 1998, 16:284-291.

Kanellopoulos., "Very high fluence collagen cross-linking as a refractive enhancement of a regressed previous astigmatic keratotomy," J Refract Surg, 29(7):504-5, 2013.

Kohlhaas et al., "Bio mechanical evidence of the distribution of cross-links in corneas treated with riboflavin and ultraviolet A light," J Cataract Refract Surg, Feb. 2006, 32:279-283

Kymionis et al., "Corneal collagen cross-linking with riboflavin and ultraviolet-A irradiation in patients with thin corneas," Am. J. Ophthalmol, 2012, 153(1): 24-28.

LaMuraglia et al., "Photodynamic therapy inhibition of experimental intimal hyperplasia: acute and chronic effects." J Vasc Surg. 19:321-331, 1994.

Lanchares et al., "Biomechanical property analysis after corneal collagen cross-linking in relation to ultraviolet Airradiation time," Graefes Arch Clin Exp Ophthalmol, 2011, 249:1223-1227.

Marcus Overhaus, et al., "Photodynamic Therapy Generates a Matrix Barrier to Invasive Vascular Cell Migration," Circ Res, 86:334-340, 2000.

Mazzotta et al., "Corneal collagen cross-linking to stop corneal ectasia exacerbated by radial keratotomy," Cornea, Feb. 2011, 30(2):225-8.

Nakayasu et al., "Distribution of types I, II, III, IV and V collagen in normal and keratoconus corneas," Ophthalmic Res, 1986, 18(1):1-10.

Raiskup-Wolf et al., "Collagen crosslinking with riboflavin and ultraviolet light in keratoconus: long-term results," J. Cataract Refract. Surg. 34(5), 796-801, 2008.

Shen et al., "Photodynamic crosslinking of proteins, I: model studies using histidine- and lysinecontaining N-(2-hydroxypropyl) methacrylamide copolymers," J Photochem Photobiol, 1996, 34:203-210.

(56) References Cited

OTHER PUBLICATIONS

Spoerl et al., "Increased resistance of crosslinked cornea against enzymatic digestion," Curr Eye Res, 29(1):35-40, 2004.
Sporl et al., "Artificial stiffening of the cornea by induction of intrastromal cross-links," Ophthalmologe, 1997, 94:902-906 (with English summary—p. 903).
Tanaka et al., "Glycation induces expansion of the molecular packing of collagen," J Mol Biol, 1988, 203:495-505.
Therapy (TAP) Study Group., "Photodynamic therapy of subfoveal choroidal neovascularization in age-related macular degeneration with verteporfin: Two-year results of 2 randomized clinical trials—TAP Report 2." Arch Ophthalmol, 119: 198-207, 2001.
Treatment of Age-Related Macular Degeneration With Photodynamic Therapy (TAP) Study Group, "Photodynamic therapy of subfoveal choroidal neovascularization in age-related macular degeneration with verteporfin: one-year results of 2 randomized clinical trials-TAP Report 1," Arch Ophthalmol, 1999, 117:1329-1345.
Wollensak and Iomdina, "Biomechanical and histological changes after corneal crosslinking with and without epithelial debridement," J Cataract Refract Surg, 2009, 35:540-546.
Wollensak et al., "Collagen fiber diameter in the rabbit cornea after collagen crosslinking by riboflavin/UVA," Cornea; 23:503-507, 2004.
Wollensak et al., "Gel electrophoretic analysis of corneal collagen after photodynamic cross-linking treatment." Cornea, 2008, 27:353-356.
Wollensak et al., "Long-term biomechanical properties of rabbit cornea after photodynamic collagen crosslinking," Acta Ophthalmol; 87:48-51, 2009. Available at: http://onlinelibrary.wiley.com/doi/10.1111/j.1755-3768.2008.01190.x/pdf. Accessed Dec. 4, 2012.
Wollensak et al., "Stress-strain measurements of human and porcine corneas after riboflavin-ultraviolet-A-induced cross-linking," J Cataract Refract Surg, 29:1780-1785, 2003.
Yoon et al., "Experimental inhibition of corneal neovascularization by photodynamic therapy with verteporfin," Curr Eye Res, 2006, 31:215-24.
Holzer et al, "Photodynamic Therapy with Verteporfin in a Rabbit Model of Corneal Neovascularization," Investigative ophthalmology & visual science, 2003, 44(7):2954-2958.
Yoon et al, "Photodynamic Therapy with Verteporfin for Corneal Neovascularization," American Journal of Ophthalmology, 2007, 144(3):390-395.
Ambati et al., "Diffusion of High Molecular Weight Compounds through Sclera," Investigative Ophthalmology & Visual Science, Apr. 2000, 41(5):1181-1185.
Lang, "Ocular drug delivery conventional ocular formulations," Advanced Drug Delivery Reviews, Aug. 1995, 16(1):39-43.

* cited by examiner

FIGs. 9A-B

METHODS FOR CROSS-LINKING CORNEAL COLLAGEN WITH VERTEPORFIN FOR THE TREATMENT OF DISORDERS OF THE EYE

CROSS-REFERENCE TO RELATED APPLICATIONS

This application is a U.S. National phase Application of PCT/US2015/017776, filed on Feb. 26, 2015, which claims priority to U.S. Provisional Patent Application No. 61/946,310, filed on Feb. 28, 2014. The contents of the foregoing are incorporated herein by reference in their entirety.

FEDERALLY SPONSORED RESEARCH OR DEVELOPMENT

This invention was made with Government support under Grant No. NIH National Eye Institute 1K08EY019686 awarded by the National Institutes of Health. The Government has certain rights in the invention.

TECHNICAL FIELD

This invention relates to corneal increasing corneal rigidity in a subject with non-thermal photodynamic therapy, and more particularly to corneal cross-linking with non-thermal photodynamic therapy with the photosensitizing compound verteporfin.

BACKGROUND

In recent years, there has been considerable interest in corneal cross-linking (CXL) as a means of halting the progression of keratoconus, a progressive, noninflammatory corneal thinning disorder that affects 1 in 2000 in the younger working-age population. The procedure involves initiation of a photochemical reaction in the corneal stroma that increases binding of collagen fibrils, resulting in increased corneal stiffness.[2-3] By stabilizing the corneal biomechanics, CXL is used to prevent or postpone the need for corneal transplant. Conventional CXL uses the "Dresden protocol" and involves removal of the central cornea epithelium followed by topical application of riboflavin solution (0.1% in 20% dextran) onto the cornea every 3 to 5 minutes for 30 minutes. The cornea is then irradiated for 30 minutes with an ultraviolet A (UVA) light at irradiance of 3 mW/cm$^2$ for a cumulative UVA delivery of 5.4 J/cm$^2$. Typically, an additional drop of riboflavin is instilled every 5 minutes during the 30 minutes of irradiation.

Photoactivation of riboflavin induces the formation of free radicals that interact with corneal proteins leading to covalent bonding within collagen fibrils. Since generation of free radicals also causes cell death, riboflavin concentration, UVA irradiance, and treatment duration have specifically chosen to minimize cellular damage and protect the corneal endothelium.[36] These parameters effectively limit CXL to the anterior 300 μm of the corneal stroma[37] and also restrict UVA CXL therapy to corneas thicker than 400 μm. Treatment of corneas less than 400 μm thick would risk damage to the cornea endothelial cells. Alternative UVA CXL protocols that either preserve the cornea or reduce radiance exposure have been proposed for treating thin corneas.[38] However, endothelial damage remains a concern and has even been reported to occur in corneas that were thicker than 400 μm pre-operatively.[39] Unwanted side effect such as stromal haze, microbial keratitis, scaring, vision loss, and others have been also reported. Because of these concerns, there is an ongoing need for improved methods for strengthening the cornea in a manner that provides greater safety, improved efficacy, and the opportunity to expand the treatment to include thin corneas.

SUMMARY

At least in part, the present invention is based on the discovery that photodynamic therapy with topical verteporfin can be used to cross-link corneal collagen and to increase the biomechanical strength and rigidity of the cornea.

In some aspects, the disclosure provides methods for increasing corneal rigidity in a subject. The methods include topically administering a composition comprising verteporfin to the cornea of a subject and irradiating the cornea with non-thermal laser (i.e., non-burning laser) light. In some embodiments, the subject undergone, or is going to undergo, a refractive surgical procedure, wherein the refractive surgical procedure is selected from the group consisting of radial keratotomy (RK), photorefractive keratectomy (PRK), and laser in-situ keratomileusis (LASIK).

In some aspects, the disclosure provides methods for cross-linking collagen in corneal tissue, the method comprising applying a topical verteporfin composition to the corneal tissue (e.g., topically administering a composition comprising verteporfin to the cornea of a subject), and irradiating the corneal tissue with non-thermal laser light.

In another aspect, the disclosure provides methods for treating a corneal ectatic disorder in a subject in need thereof, comprising topically applying verteporfin to the cornea of a subject in need thereof (e.g., topically administering a composition comprising verteporfin to the cornea of a subject), and irradiating the cornea with a with light emitted from a non-thermal laser. In some embodiments, the corneal ectatic disorder is selected from the group consisting of keratoconus, pellucid marginal degenearation, or ectasia developed following refractive surgical procedure, wherein the refractive surgical procedure is radial keratotomy (RK), photorefractive keratectomy (PRK), or laser in-situ keratomileusis (LASIK).

In yet another aspect, the disclosure provides methods for increasing rigidity of the cornea following refractive surgical procedure, comprising topically administering to the cornea of a patient who has undergone, or is going to undergo, a refractive surgical procedure a composition comprising verteporfin, and irradiating the cornea with non-thermal laser light. In some embodiments, the refractive surgical procedure is selected from the group consisting of radial keratotomy (RK), photorefractive keratectomy (PRK), and laser in-situ keratomileusis (LASIK).

The methods provided herein include topically administering a composition comprising verteporfin to the cornea of a subject. In some embodiments, the verteporfin composition is a lotion, gel, cream, ointment, solution, spray, paste or aerosol composition. In some embodiments, the verteporfin composition comprises 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, or 10.0 mg/ml of verteporfin. Topically administering a composition comprising verteporfin to the cornea of a subject may comprise soaking the cornea with a verteporfin solution.

In some embodiments, the methods provided herein include irradiating the corneal with non-thermal laser light to promote cross-linking of collagen in the cornea. In some aspects, the non-thermal laser light has a wavelength of 687 nm to 693 nm, including, for example a wavelength of 689 nm. The irradiating step is performed for a time sufficient to induce cross-linking of collagen and increase rigidity of the cornea. In some embodiments, the non-thermal laser light has an intensity in a range of 200 mW/cm² to 650 mW/cm², or in a range of 575 mW/cm² to 625 mW/cm².

In some embodiments, the composition comprising verteporfin is administered to the cornea one to twenty minutes, one to ten minutes, ten to twenty minutes, two to nine minutes, three to seven minutes, four to six minutes, or four to five minutes prior to irradiating the corneal with a non-thermal laser. In some embodiments, the methods for increasing corneal rigidity in a subject provided herein comprise repeating both the administering and irradiating steps at least one, at least two, at least three, at least four, at least five, at least six, or at least seven additional times. In some embodiments, the methods provided herein comprise repeating both the administering and irradiating steps at least one, at least two, at least three, at least four, at least five, at least six, or at least seven additional times; or comprise repeating the administering step at least one, at least two, at least three, at least four, at least five, at least six, or at least seven additional times prior to the irradiating step.

In some embodiments, the methods provided herein include administering the verteporfin composition at least once, at least twice, at least three, at least four, at least five, at least six, or at least seven times to the corneal tissue periodically during the irradiating step.

The section headings used herein are for organizational purposes only and are not to be construed as limiting the described subject matter in any way. When definitions of terms in incorporated references appear to differ from the definitions provided in the present teachings, the definition provided in the present teachings shall control. In this application, the use of the singular includes the plural unless specifically stated otherwise. Also, the use of "comprise," "comprises," "comprising," "contain," "contains," "containing," "include," "includes," and "including" are not intended to be limiting. It is to be understood that both the foregoing general description and the following detailed description are exemplary and explanatory only and are not restrictive of the invention. The articles "a" and "an" are used herein to refer to one or to more than one (i.e., to at least one) of the grammatical object of the article.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DETAILED DESCRIPTION

Photodynamic therapy (PDT) is an evolving technique for localized control of diseased tissue with light after prior administration of a photosensitizing agent and in the presence of oxygen. PDT combines a photosensitizing agent, light, and oxygen to generate oxygen-free radicals that cause tissue changes. Verteporfin is a benzoporphyrin derivative monoacid ring A photosensitizer that is activated upon exposure to 689 nm nonthermal laser. PDT with verteporfin is commercially-available and is administered intravenously to induce focal ablation of pathologic vessels and is FDA-approved for the treatment of chorioretinal diseases, such as subfoveal choroidal neovascularization in age-related macular degeneration. In general, PDT is thought to cause focal damage to living cells without affecting non-living tissue, such as collagen that makes up most of the cornea stroma. However, there have been several reports of PDT used to induce collagen-to-collagen cross-linking in non-ocular structures (vascular, skin, bone, and others14-20). Given these reports, the inventors set out to explore the use of cornea collagen crosslinking with PDT and assess the biomechanical effect it has on the cornea.

Figure 1:
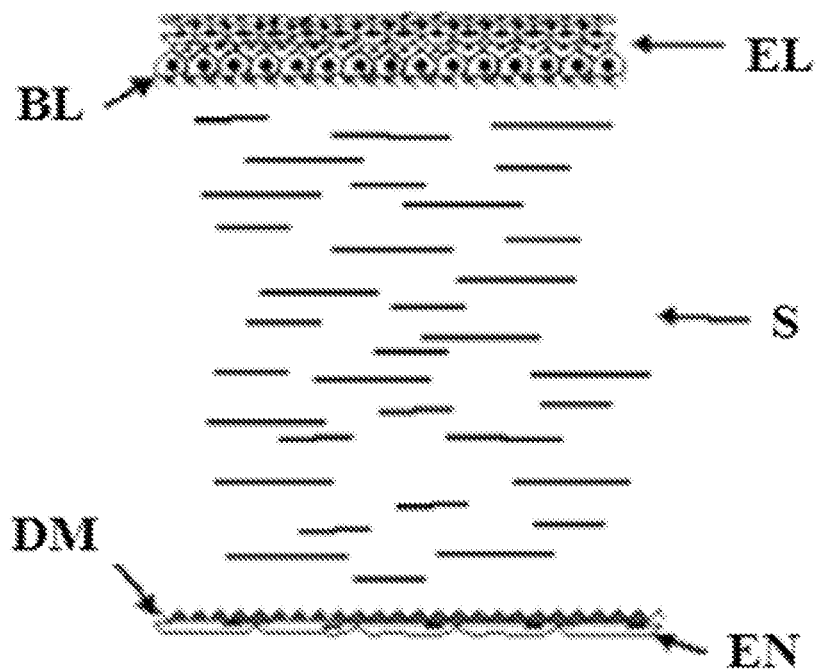
FIG. 1 is a cross-sectional view of the cornea showing the several histological layers of the cornea.

The present disclosure is based, in part, on the discovery that PDT with topical verteporfin can be used to crosslink cornea collagen and to increase the biomechanical strength of the cornea. The cornea has an outer (anterior) epithelial layer ("EL"), an inner (posterior) endothelium ("EM") and a relatively thick stroma ("S") positioned between the epithelial layer and endothelium (FIG. 1). A thin, smooth membrane, known as Bowman's Layer ("BL"), lies between the epithelial layer and the anterior surface of the stroma (FIG. 1). Another thin membrane, known as Descemet's Layer ("DL"), lies between the posterior surface of the stroma and the endothelium (FIG. 1). The stroma, as well as Bowman's Layer, contains strong collagen fibers which define the shape of the cornea. The collagen fibers within the stroma are arranged in a regular, geometric fashion which provides the needed transparency.

About 120 million people in the United States wear eyeglasses or contact lenses to correct nearsightedness, farsightedness, or astigmatism. These vision disorders—called refractive defects—affect the cornea and are the most common of all vision problems in this country. The most common types of refractive defects are myopia, hyperopia, presbyopia, and astigmatism. Myopia (nearsightedness) is a condition where objects up close appear clearly, while objects far away appear blurry. With myopia, light comes to focus in front of the retina instead of on the retina. Hyperopia (farsightedness) is a common type of refractive defects where distant objects may be seen more clearly than objects that are near. However, people experience hyperopia differently. Some people may not notice any problems with their vision, especially when they are young. For people with significant hyperopia, vision can be blurry for objects at any distance, near or far. Astigmatism is a condition in which the eye does not focus light evenly onto the retina, the light-sensitive tissue at the back of the eye. This can cause images to appear blurry and stretched out. Presbyopia is an age-related condition in which the ability to focus up close becomes more difficult. As the eye ages, the lens can no longer change shape enough to allow the eye to focus close objects clearly. Refractive defects are usually corrected by eyeglasses or contact lenses. Although eyeglasses or contact lenses are safe and effective methods for treating refractive defects, refractive surgical procedures are becoming an increasingly popular option. Refractive surgery aims to change the shape of the cornea permanently. This change in eye shape restores the focusing power of the eye by allowing the light rays to focus precisely on the retina for improved vision.

There are currently several different refractive surgical procedures to correct refractive defects of the eye. In radial keratotomy (RK), several deep incisions are made in a radial pattern around the cornea, so that the central portion of the cornea flattens. Although this can correct the patient's vision, it also weakens the cornea, which may continue to change shape following the surgery. Refractive surgical procedures using an excimer laser is presently conducted in one of two ways: photorefractive keratectomy (PRK) and Laser In situ Keratomileusis (LASIK). In the PRK technique, the laser beam is applied directly to the patient's corneal surface. The laser system removes the epithelial basement membrane and Bowman's membrane, leaving the stroma uncovered. The stroma will later be covered with new epithelial cells during the healing process, which takes a few days. One of the shortcomings of the PRK technique is that the Bowman layer or membrane is destroyed by the direct corneal application of the laser beam. Regression and corneal haze can occur following PRK.

The LASIK technique involves the use of a microkeratome, which makes an access cut across the anterior portion of the cornea forming an epithelial-stromal flap. The flap is flipped back on its hinge, and the underlying stroma ablated. The flap allows the corneal stroma to be exposed for ablation by the laser beam that is appropriate to correct the patient's refractive defect. Following the laser application, the corneal flap is returned to its initial position.

Each of these refractive surgical procedures may reduce the eye's biomechanical rigidity resulting in post-operative ectasia (e.g., post-LASIK ectasia, post-PRK ectasia, post-RK ectasia).

Keratoconus is another condition in which the rigidity of the cornea is decreased, causing the cornea to thin and change to a more conical shape than the more normal gradual curve. Keratoconus, a progressive thinning of the cornea, it is the most common corneal dystrophy in the U.S., affecting one in every 2,000 Americans. It is more prevalent in teenagers and adults in their 20s. Keratoconus arises when the middle of the cornea thins and gradually bulges outward, forming a rounded cone shape. This abnormal curvature changes the cornea's refractive power, producing moderate to severe distortion (astigmatism) and blurriness (nearsightedness) of vision. Keratoconus may also cause swelling and a sight-impairing scarring of the tissue. Keratoconus can cause substantial distortion of vision, with multiple images, streaking and sensitivity to light all often reported by the patient.

Because both keratoconus and post-operative ectasia involve reduced corneal rigidity, relief from each disease could be provided by methods of increasing the rigidity of the cornea. For example, methods which increase the rigidity of the cornea can be used to treat post-operative ectasia. Optionally, the treatment can be administered to a patient who plans to undergo a refractive surgical procedure as a prophylactic therapy. In other cases, the treatment can be administered during the surgical procedure itself. In still other situations, the treatment may not be initiated until after the refractive surgical procedure. Of course, various combinations of treatment before, during, and after the surgery are also possible.

Verteporfin (trade name Visudyne®, Novartis), a benzoporhyrin derivative, is a light-activated drug used in photodynamic therapy (PDT). Once verteporfin is when stimulated by nonthermal red light with a wavelength of ~689 nm (±3 nm) in the presence of oxygen, highly reactive, short-lived reactive oxygen radicals are generated.

Visudyne® (verteporfin for injection) is currently used as a photosensitizer for photodynamic therapy to eliminate the abnormal blood vessels in the eye and is indicated for the treatment of predominantly classic subfoveal choroidal neovascularization due to age-related macular degeneration, pathologic myopia, or presumed ocular histoplasmosis. Visudyne® is administered intravenously for approximately ten minutes. Following injection, verrteporfin is transported in the plasma primarily by lipoproteins and accumulates in these abnormal blood vessels. After approximately fifteen minutes, the treatment site is activated with laser light having a wavelength of 689 nm±3 nm at 150-600 mW/m$^2$. Light activation of verteporfin results in local damage to neovascular endothelium, resulting in vessel occlusion. Damaged endothelium is known to release procoagulant and vasoactive factors through the lipo-oxygenase (leukotriene) and cyclo-oxygenase (eicosanoids such as thromboxane) pathways, resulting in platelet aggregation, fibrin clot formation and vasoconstriction.

Photodynamic therapy (PDT) is a non-invasive medical procedure used for the treatment of various diseases. PDT involves the administration of a photosensitizing compound (e.g., verteporfin) that concentrates around a portion of tissue. Thereafter the tissue that is concentrated with the photosensitizing compound is irradiated. For the verteporfin, PDT comprises irradiating the tissue that is concentrated with verteporfin with laser light having a wavelength of approximately 689 nm at 150-600 mW/m$^2$.

The invention provides a laser system configured for administering therapy to a patient. The laser system includes a laser source capable of emitting a non-thermal laser light having a wavelength of approximately 689 nm±3 nm at 150-600 mW/m2. There are several laser systems suitable for delivering laser light to a photosensitizing compound (e.g., verteporfin) such as Opal Photoactivator (Coherent, Inc., Santa Clara, Calif.), ML7710-PDT laser system from Modulight Inc., Diomed 630 PDT Laser Model T2USA-P990021, Zeiss 690s PDT Ophthalmic Laser refurbished w SL120 Slit Lamp, table and lenses.

In some aspects, the laser system is configured for targeting the non-thermal laser light to a depth within the cornea in a range of approximately 50 microns to 500 microns, 100 microns to 450 microns, 150 microns to 400 microns, 200 microns to 350 microns, 250 microns to 300 microns, 50 microns to 250 microns, or 250 microns to 500 microns.

The present disclosure provides methods for increasing the rigidity of the cornea (i.e., cross-linking collagen in corneal tissue), comprising applying a composition comprising verteporfin to the cornea and irradiating the cornea with light emitted from a non-thermal laser. In some embodiments, applying verteporfin to the cornea comprises applying a verteporfin composition to the cornea using, for example, a topical verteporfin composition. Thus, the present disclosure provides methods that include topical ocular administration, e.g., application of verteporfin, for example, by eye drops or gel-like formulations directly onto the eye. Thus, the disclosure provides pharmaceutical compositions of verteporfin that are formulated for topical administration to the eye. The pharmaceutical composition contemplated herein comprises an effective amount of verteporfin, or a physiologically acceptable salt thereof, and at least one pharmaceutically acceptable carrier or excipient. More particularly, the pharmaceutical compositions provided herein are formulated using any pharmaceutically acceptable carriers or excipients suitable for topical administration to the eye surface. For example, pharmaceutical composition may be formulated in a solution containing polyethylene glycols, in an oily solution, in an anionic emulsion or in a cationic emulsion. Any pharmaceutically acceptable carrier or excipient, or combination thereof, appropriate to verteporfin may be used, thus, the photoactive compound may be administered as a lotion, gel, cream, ointment, solution (e.g., an aqueous solution), liposome, spray, or aerosol containing verteporfin. In some embodiments, the topical verteporfin composition is a verteporfin solution. In some embodiments, applying verteporfin to the cornea comprises soaking the cornea with a verteporfin solution.

A "pharmaceutical composition" is defined herein as comprising an effective amount of verteporfin, or physiologically acceptable salt thereof, and at least one pharmaceutically acceptable carrier or medium. The pharmaceutical composition may be used in a method for treatment of the human or animal's eye.

Pharmaceutical compositions may be in the form of liquid or semi-solid dosage preparations. For example, verteporfin compositions may be formulated as solutions, dispersions, suspensions, emulsions, mixtures, lotions, liniments, jellies, ointments, creams, pastes, gels, hydrogels, aerosols, sprays, foams, and the like. In certain preferred embodiments of the present invention, compositions are formulated as lipophilic solutions, anionic emulsions or cationic emulsions.

Pharmaceutically acceptable carriers, vehicles, and/or excipients suitable for incorporation into topical compositions can be routinely selected for a particular use by those skilled in the art. Such carriers, vehicles and excipients include, but are not limited to, solvents, buffering agents, inert diluents, suspending agents, dispersing agents or wetting agents, preservatives, stabilizers, chelating agents, emulsifying agents, anti-foaming agents, gel-forming agents, humectants, and the like.

The term "topical formulation" and "topical composition" are used herein interchangeably. They refer to a composition formulated such that the active ingredient(s) of the composition may be applied for direct administration to the surface of the eye and from which an effective amount of the active ingredient(s) is released. Examples of topical formulations include, but are not limited to lotions, gels, creams, ointments, solutions (e.g., an aqueous solution), sprays, pastes, and the like.

The term "topical", when used herein to characterize the delivery, administration or application of a composition of the present invention, is meant to specify that the composition is delivered, administered or applied directly to the site of interest (i.e., to the eye) for a localized effect.

Methods of formulating suitable topical compositions are known in the art, see, e.g., *Remington: The Science and Practice of Pharmacy*, 21st ed., 2005; and the books in the series *Drugs and the Pharmaceutical Sciences: a Series of Textbooks and Monographs* (Dekker, N.Y.).

It is also within the scope of the present invention to combine any of the methods and any of the compositions disclosed herein with one or more pharmaceutically active substances. A pharmaceutically active substance includes, but is not limited to, small molecules, peptides, antibodies, ribozymes, antisense oligonucleotides, chemotherapeutic agents and radiation. For example, the pharmaceutical compositions of provided herein may optionally further comprise at least one additional pharmaceutically active substance, which can be selected, for example, from the group consisting of an antimicrobial agent, an antibacterial agent, an antiviral agent, an antifungal agent, an antibiotic, an anti-inflammatory agent, an antiseptic agent, an antihistamine agent, an immunostimulating agent, a dermatological agent, an intraocular pressure lowering agent, and any combination thereof.

In some embodiments, the verteporfin composition (e.g., a verteporfin solution) comprises 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, or 10.0 mg/ml of verteporfin. In some embodiments, the verteporfin composition comprises 6.0 mg/ml of verteporfin.

In some embodiments, the methods provided herein further comprise administering the verteporfin composition (e.g., a topical verteporfin composition) 1, 2, 3, 4, 5, 6, 7, 8, 9, 10 or more times before irradiating the corneal tissue with non-thermal laser light. For example, the verteporfin composition (e.g., a topical verteporfin composition) can be applied to the corneal tissue once, twice, three, four, five, six, seven, eight, nine, ten or more times, with the corneal tissue being irradiating following each application of the verteporfin composition. Alternatively, the verteporfin composition (e.g., a topical verteporfin composition) can be applied to the corneal tissue once, twice, three, four, five, six, seven, eight, nine, ten or more times prior to irradiation with non-thermal laser light.

In some embodiments, the verteporfin composition is applied to the corneal tissue at least 1, 2, 3, 4, 5, 6, 7, 8, 9, 10, 11, 12, 13, 14, 15, 16, 17, 18, 19, 20 or more minutes prior to irradiating the corneal tissue with a non-thermal laser.

In another aspect, the disclosure provides methods for the treatment of eye diseases and conditions, in particular eye diseases and conditions that affect the surface of the eye, such as inflammatory conditions. Such methods generally comprise a step of topically administering to a subject's eye surface, an effective amount of a pharmaceutical composition of the invention.

After verteporfin has been administered to the corneal tissue, the corneal tissue is irradiated with non-thermal laser light at a wavelength absorbed by verteporfin. In some embodiments, the non-thermal laser emits light in a wavelength range from 685 nm to 695 nm, from 686 nm to 694 nm, from 687 nm to 693 nm, from 688 nm to 692 nm, from 689 nm to 699 nm, or from 689 nm to 690 nm. In some embodiments, the non-thermal laser emits light in at wavelength of 689 nm.

The irradiance intensity typically varies from 150-900 mW/cm$^2$, such as, for example with the range between 200-650 mW/cm$^2$, or with the range between 500-600 mW/cm$^2$. However, the use of higher irradiances may be selected as effective and having the advantage of shortening treatment times.

The corneal tissue can be irradiated with a continuous exposure of non-thermal laser light. For example, the corneal tissue can be irradiated for a continuous period of 10 to 600 seconds, 30 seconds to 600 seconds, 60 seconds to 540 seconds, 90 seconds to 480 seconds, 120 seconds to 420 seconds, 180 seconds to 360 seconds, or 240 seconds to 300 seconds. The corneal tissue can be irradiated with 1, 2, 3, 4, 5 or 6 bursts of non-thermal laser light exposure, wherein each burst is 1 to 90 seconds, or 10 to 60 seconds in duration.

In some aspects, the corneal tissue is irradiated with a non-thermal laser following application of the verteporfin composition for a selected time period to promote cross-linking of collagen in the corneal tissue. The selected time period can be, for example, 1 to 30 minutes. In some embodiments, the selected time period is between 3 to 17 minutes, between 5 minutes to 15 minutes, between 5 to 10 minutes, or between 5 minutes to 8 minutes. In some embodiments, the selected time period is greater than or equal to 1, 2, 3, 4, 5, 6, 7, 8, 9, 10, 11, 12, 13, 14, 15, 16, 17, 18, 19, 20 or more minutes. In some embodiments, the selected period of time is less than or equal to 25, 20, 19, 18, 17, 16, 15, 14, 13, 12, 11 or fewer minutes. In some embodiments, more verteporfin composition is applied to the corneal tissue periodically during the non-thermal laser irradiation period. In some embodiments, the verteporfin solution is applied to the corneal tissue periodically during the non-thermal laser irradiation period every one to three minutes.

In some aspects, the combination of a photosensitizing agent such as verteporfin and non-thermal laser light produces collagen cross-linking in eye tissue such as corneal tissue. Thus, the invention provides methods for collagen cross-linking in corneal tissue. Collagen cross-linking is used for the treatment of multiple ophthalmic disorders. In some cases, collagen cross-linking may also be combined with other treatments to improve corneal strength or optical refraction. Collagen cross-linking limits deterioration of vision, increases unaided and uncorrected vision, and may reduce the need for corneal transplantation.

The methods described herein include methods for increasing the rigidity of, and therefore increasing the biomechanical strength of, the cornea to treat ophthalmic disorders involving reduced corneal rigidity. In some embodiments, corneal rigidity (e.g., corneal hysteresis) can be measured on live eyes using an Ocular Response Analyzer. Corneal rigidity can be measured ex vivo using the methods outlined below. In some embodiments, the ophthalmic disorder is keratoconus and/or post-operative ectasia. Generally, the methods include administering a therapeutically effective amount of verteporfin as described herein, to a subject who is in need of, or who has been determined to be in need of, such treatment. The methods include administering verteporfin to a selected region of a cornea of the eye and initiating crosslinking activity in the selected region by activating the verteporfin with photodynamic therapy using a nonthermal laser.

The terms "treat" or "treating," as used herein, refers to partially or completely alleviating, inhibiting, ameliorating, and/or relieving the disease or condition from which the subject is suffering. In some instances, treatment can result in the continued absence of the disease or condition from which the subject is suffering.

An "effective amount" is an amount sufficient to effect beneficial or desired results. For example, a therapeutic amount is one that treats the disorder or achieves a desired therapeutic effect. This amount can be the same or different from a prophylactically effective amount, which is an amount necessary to prevent onset of disease or disease symptoms. An effective amount can be administered in one or more administrations, applications or dosages. A therapeutically effective amount of a therapeutic compound (i.e., an effective dosage) depends on the therapeutic compounds selected. The compositions can be administered from one or more times per day to one or more times per week; including once every other day. The skilled artisan will appreciate that certain factors may influence the dosage and timing required to effectively treat a subject, including, but not limited to, the severity of the disease or disorder, previous treatments, the general health and/or age of the subject, and other diseases present. Moreover, treatment of a subject with a therapeutically effective amount of the therapeutic compounds described herein can include a single treatment or a series of treatments.

Dosage, toxicity, and therapeutic efficacy of the therapeutic compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds that exhibit high therapeutic indices are typically preferred. While compounds that exhibit toxic side effects may be used, care should be taken to design a delivery system that targets such compounds to the site of affected tissue to minimize potential damage to uninfected cells and, thereby, reduce side effects.

The data obtained from cell culture assays and animal studies can be used in formulating a range of dosages for use in humans. The dosage of such compounds lies preferably within a range of circulating concentrations that include the ED50 with little or no toxicity. The dosage may vary within this range depending upon the dosage form employed and the route of administration utilized. For any compound used in the methods of the inventions described herein, the therapeutically effective dose can be estimated initially from cell culture assays. A dose may be formulated in animal models to achieve a circulating plasma concentration range that includes the IC50 (i.e., the concentration of the test compound that achieves a half-maximal inhibition of symptoms) as determined in cell culture. Such information can be used to more accurately determine useful doses in humans. Levels in plasma may be measured, for example, by high performance liquid chromatography.

The term "subject" as used herein refers to a mammal. A subject therefore refers to, for example, dogs, cats, horses, cows, pigs, guinea pigs, and the like. The subject can be a human. When the subject is a human, the subject may be referred to herein as a patient.

In general, methods include selecting a subject at risk for or with a condition or disease. In some instances, the subject's condition or disease can be treated with a pharmaceutical composition disclosed herein. For example, in some instances, methods include selecting a subject with an ophthalmic disorders (e.g., an ectatic disorder) involving reduced corneal rigidity, e.g., wherein the ophthalmic disorders involving reduced corneal rigidity.

In some instances, treatments methods can include a single administration, multiple administrations, and repeating administration as required for the prophylaxis or treatment of the disease or condition from which the subject is suffering. In some instances treatment methods can include assessing a level of disease in the subject prior to treatment, during treatment, and/or after treatment. In some instances, treatment can continue until a decrease in the level of disease in the subject is detected.

Following administration, the subject can be evaluated to detect, assess, or determine their level of disease. In some instances, treatment can continue until a change (e.g., reduction) in the level of disease in the subject is detected. In some aspects, the subject can be evaluated to detect, assess, or determine the amount of collagen cross-linking resulting from the activation of verteporfin.

The invention also provides methods for cross-linking collagen in corneal tissue following a refractive surgical procedure, comprising topically administering to the eye of a patient who has undergone a refractive surgical procedure a composition comprising verteporfin; and irradiating the eye with non-thermal laser light.

The invention also provides methods for treating keratoconus in a patient in need there of comprising topically administering to the eye of a patient a composition comprising verteporfin and irradiating the eye with non-thermal laser light.

In some aspects, the invention also provides methods for the treatment of ophthalmic disorders, such as ectatic diseases, including, for example, keratoconus, post-operative ectasia (e.g., post-LASIK ectasia, post-PRK ectasia, post-RK ectasia), and pellucid marginal degeneration, the method comprising cross-linking collagen in corneal tissue to increase rigidity of the cornea. The treatment can be prophylactic, contemporaneous with a surgical procedure (e.g., a refractive surgery) postoperative, or can involve multiple administrations during one or more of those time points.

The invention also provides methods for treating an ectatic disease in a patient in need thereof, comprising topically administering verteporfin to the cornea of a patient in need thereof and irradiating the cornea with a light emitted from a non-thermal laser.

The methods described herein include method for increasing rigidity of the cornea following refractive surgical procedure, comprising topically administering to the cornea of a patient who has undergone a refractive surgical procedure a composition comprising verteporfin; and irradiating the cornea with non-thermal laser light. In some embodiments, the disclosure provides methods following surgical treatment or trauma to eye tissue. In some embodiments, the methods disclosed herein are used to treat ocular wounds related to corneal cataract incisions, corneal or scleral lacerations (trauma), relaxing incisions and other surgical wounds resulting from surgery to adjust refractive properties of the cornea, flaps or other incisions from LASIK and other refractive surgeries, scleral incisions, sealing of conjunctival grafts after pterygium surgery, and keratoplasties. In some embodiments, the systems and methods for ocular wound sealing as described herein reduce or adjust astigmatism after cataract or other ocular surgery

EXAMPLES

The invention is further described in the following examples, which do not limit the scope of the invention described in the claims.

The inventors studied the ability of verteporfin-red non-thermal laser (V-NTL) to increase the strength of the cornea. The strength of the cornea was demonstrated through biological studies (resistance and enzymatic degradation) and through mechanical stress-strain studies. Gross observation and confocal microscopy were performed on treated and untreated corneas.

Material and Methods:

Human research corneas were obtained from Tissue Bank International (Baltimore, Md.) and North Carolina Eye Bank (Winston-Salem, N.C.). Riboflavin 5'-phosphate sodium salt hydrate, 20% (w/w) dextran solution (from *Leuconostoc mesenteroides*) and collagenase A (from *Clostridium histolyticum*, E.C. 3.4.24.3) were obtained from Sigma Aldrich (St. Louis, Mo.). Barron® artificial anterior chambers were purchased from Katena Eye Instruments (Denville, N.J.). The VEGA LED-based UV emitter was purchased from Costruzione Strumenti Oftalmici (Firenze, Italy). The Excells E24 incubator shaker series was purchased from New Brunswick Scientific (Enfield, Conn.).

Tissue Preparation

The corneas were obtained in OptiZol® solution and stored at 4° C. until use. All experiments were performed within 2 weeks from the date of death of the donor. Each cornea was fitted into a Barron® artificial anterior chamber with normal balanced salt solution followed by mechanical removal of 8 mm of the central corneal epithelium with a blunt blade.

Riboflavin and UVA Treatment

Conventional riboflavin-UVA (R+UVA) crosslinking was performed in an ex vivo fashion according to the Dresden protoco.[1-2] 50 mg of riboflavin 5'-phosphate was added to 50 mL of dextran (w/w) and mixed thoroughly to make 0.1% riboflavin (1 mg/mL) solution. All solutions were covered in aluminum foil for protection from room UV light and stored at 4° C. until use. Riboflavin solution was topically administered every 5 minutes onto the surface of the de-epithelialized cornea for total instillation period of 30 minutes. UVA 370 nm light (X-Vega, Sooft SPA) was then focused onto the surface of the cornea at an irradiance of 3 mW/cm$^2$ (5.4 J/cm$^2$ fluence) for 5 minutes. The five-minute UVA exposure sequence was repeated 5 more times for a total UVA exposure time of 30 minutes. Prior to each 5-minute UVA treatment sequence, one drop of balanced salt solution and one drop of riboflavin were administered onto the surface of the cornea.

Verteporfin and Non-Thermal Laser Treatment

Each de-epithelialized cornea was placed on a Barron® artificial anterior chamber and underwent a treatment protocols (below) that included either topical verteporfin solution alone, non-thermal laser alone, or a combination of both topical verteporfin and non-thermal laser. Verteporfin solution was applied topically using the same formulation that is administered intravenously for the treatment of choroidal neovascularization[3-8] (6 mg/mL, Visudyne; Novartis Ophthalmics AG, Hettingen, Switzerland). A 689 nm wavelength non-thermal laser (Opal Photoactivator; Coherent Inc., Santa Clara, Calif.) was applied using a spot size of 7 mm at a power intensity of 600 mW/cm$^2$.

1. Topical verteporfin (V), without laser: Verteporfin solution was topically administered onto the surface of a de-epithelialized cornea every minute for 15 minutes. The tissue was not exposed to laser therapy.

2. Irradiation with non-thermal laser (NTL), without verteporfin: The central cornea was exposed to NTL for a one minute treatment sequence that was repeated 6 times for a total of NTL exposure time of 6 minutes. Between each treatment sequence, one drop of balanced salt solution was administered onto the surface of the cornea to maintain hydration.

3. Combined treatment of verteporfin with non-thermal laser for one treatment sequence (V+NTL-1): Verteporfin, which was prepared at a dose of 6 mg/ml (one drop per minute) was applied onto the de-epithelialized corneas every minute for fifteen minutes followed by one NTL treatment sequence. A 689 nm nonthermal laser light was delivered directly over a cornea with spot sizes (7 mm) at a power intensity of 600 mW/cm$^2$ for one minute only.

4. Combined treatment of Verteporfin with Non-Thermal Laser Therapy for six treatment sequences (V+NTL-6): Verteporfin solution (6 mg/ml) was topically applied every minute for fifteen minutes followed by six NTL sequences. One drop of balanced salt solution and one drop of verteporfin was administered between each treatment sequence.

Enyzmatic Digestion

Resistance to collagenase digestion was assessed by submerging cornea buttons in collagenase A and measuring the time until complete digestion.[9-14] The de-epithelialized corneas were divided into the following subgroups (n=5 per subgroup): (1) Topical verteporfin (V), without laser; (2) Irradiation with non-thermal laser (NTL), without verteporfin; (3) Combined treatment of verteporfin with non-Thermal Laser Therapy for one treatment sequence (V+NTL1); (4) Combined treatment of verteporfin with non-Thermal Laser Therapy for six treatment sequences protocol (V+NTL6); (5) Riboflavin-UVA cross-linked (R+UVA) corneas; and (6) Untreated de-epithelialized corneas Z.

All corneas were trephined into 8.5-mm buttons, placed in clear glass vials, and incubated in 1 mL 0.3% collagenase. A solution (3 mg/mL in phosphate-buffered solution) at 37° C. rotating at 150 rotations-per-minute. The corneas were observed hourly for the first 12 hours, and then every 30 minutes until the corneal buttons were completely dissolved. The time to total dissolution of the corneal button was recorded and all groups were compared to untreated corneas.

Biomechanical Testing

The biomechanical properties of untreated corneas and corneas treated with R+UVA and V+NTL6 were measured using gross observation, compression, creep and tensile strength testing. The corneas were stored in Optisol GS and refrigerated at 4° C. until the time of testing.

Compression Testing

Figure 2:
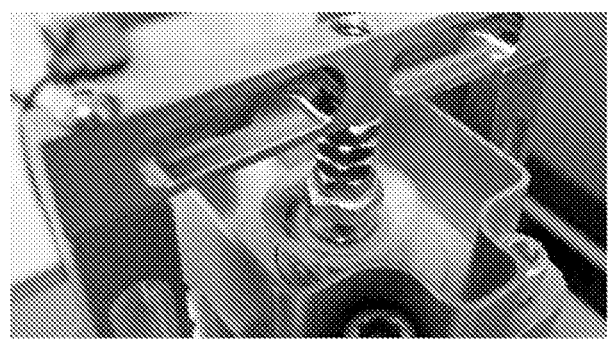
FIG. 2 is a photograph demonstrating sample position during compression testing on the Q800 DMA prior to adding 1×PBS solution.

Compression testing was performed using a Q800 DMA (TA instruments). The tissue was placed within a submersion clamp and centered beneath a custom 8 mm diameter compression plate, as shown in FIG. 2. The submersion clamp was filled with 1× phosphate buffered saline (PBS) solution to prevent the sample from drying out during the test. The compression plate was brought into contact with the central corneal tissue (i.e., the sclera was not compressed) and the sample thickness was measured as the plate separation at a preload force of 0.1 N. The sample was then compressed at a rate of 7.5 N/min up to a force of 15 N. This endpoint was selected based on previous work that suggested that this force would still be well below the point at which permanent damage is caused to the sample.

Creep Testing

After a force of 15 N was reached at the end of the compression test, a short-duration creep test was performed. The sample was held under a constant force of 15 N and the strain was measured over a period of 4.25 minutes.

Tensile Strength Testing

A rectangular strip of corneal tissue (approximately 3 mm wide and 14 mm long) was cut from each sample with a scalpel. The corneal strips were individually clamped between the two jaws of a microcomputer-controlled biomaterial tester (Minimat, Rheometriv Scientific GmbH).[15-20] Tensile testing was performed using a Shimadzu AGS-X (Cambridge Polymer Group, Inc. 56 Roland St suite 310, Boston, Mass. 02129, United States) load frame equipped with a 50 N load cell and pneumatic grips, which were lined with sandpaper for prevent tissue slippage. The pneumatic grips compensated for any dimensional change as the samples were stretched and allowed a fixed grip pressure of 35 pressure per square inch (psi) to be applied. The initial grip separation was set to 4.5 mm and tested at a rate of 0.025 mm/sec until failure. The strain ($\varepsilon$) was then increased linearly at a certain velocity, and the relative stress (s) was measured.

Data Analysis

Statistical analysis was performed using Graphpad Instat 3.10. Normality was tested using the Kolmogorov-Smirnov test, and non-parametric tests were used when indicated. One-way analysis of variance (ANOVA) and Kruskal-Wallis test were used to compare times to total dissolution between all groups. Mann-Whitney U-statistics was used for comparing non-parametric non-matched groups. The tests were performed using a 2-tailed p-value of 0.05. The results were reported as mean±standard deviation.

Example 1. Gross Examination

Figure 3:
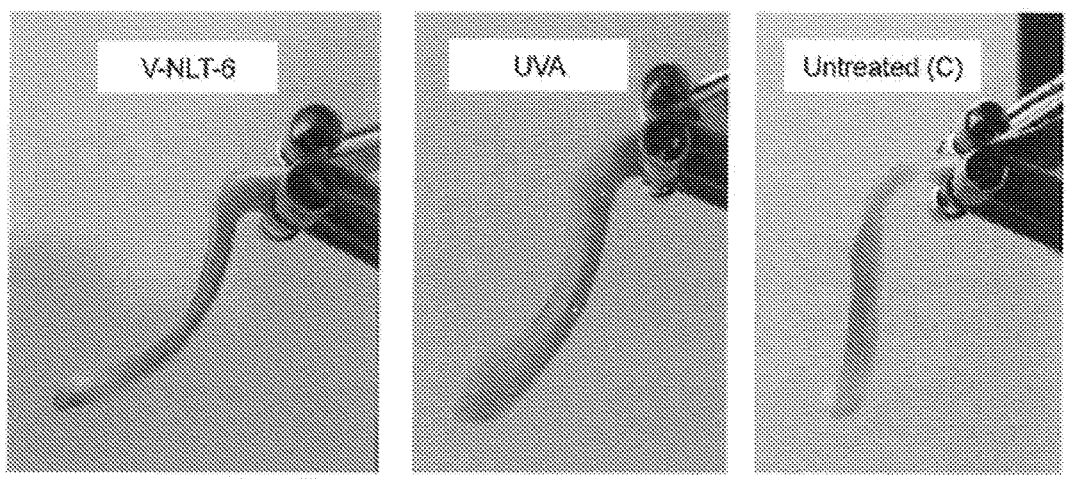
FIG. 3 provides representative images of corneal curvature for each sample group (C)=untreated corneas that served as primary controls; (V-NLT-6)=combined treatment of topical verteporfin with non-thermal laser therapy for six treatment sequences; and (UVA)=conventional cross-linking through combined topical riboflavin (0.1% riboflavin/20% dextran) and irradiated with ultraviolet light type A ($\lambda$=370 nm, irradiance=3 mW/cm²) for 30 minutes.

On gross examination, corneas treated by topical verteporfin followed by six sequence treatments of non-thermal laser (V+NTL6) and corneas treated by riboflavin and UVA light using the Desdon protocol (R+UVA) were observed to have a much more rigidity than untreated corneas. For example, when cornea strips were placed horizontally in a clamp, the tissue treated by V+NTL$_6$ and by R+UVA were noted to have a more pronounced curvature than the untreated control group (FIG. 3).

Example 2. Resistance to Enzymatic Digestion

Figure 4:
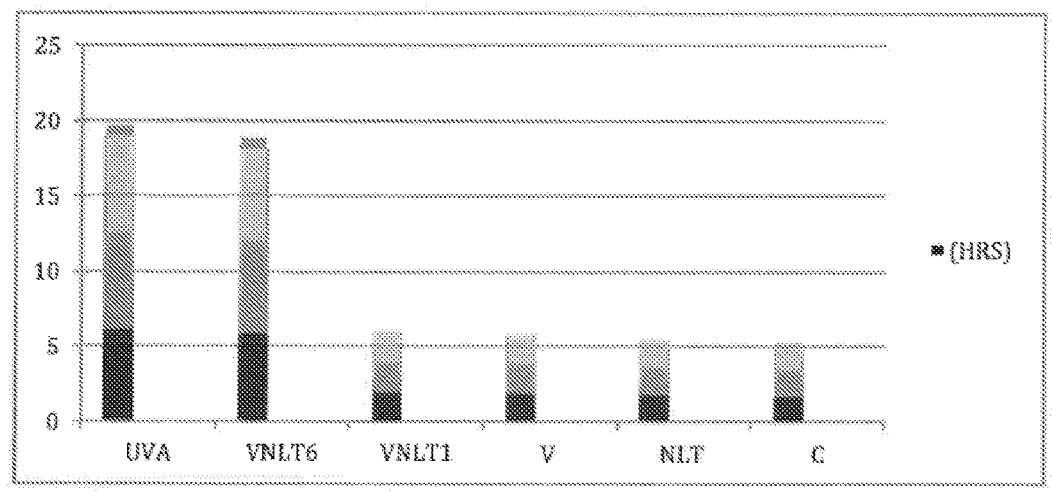
FIG. 4 is a graph demonstrating time to dissolution study ((UVA)=conventional cross-linking through combined topical riboflavin (0.1% riboflavin/20% dextran); (V-NLT-6) =combined treatment of topical verteporfin with non-thermal laser therapy for six treatment sequences; (V-NLT-1) =combined treatment of topical verteporfin with non-thermal laser therapy following a single treatment; (V)=topical verteporfin without non-thermal laser therapy; (NTL)=Irradiation with non-thermal laser, without verteporfin; and (C)=untreated corneas that served as primary controls)

Untreated corneas (C) dissolved in collagenase A at 5.47 h±0.21 hours (FIG. 4, Table 1). R+UVA treated corneas demonstrated a slower rate of dissolution than untreated corneas (20.06 h±1.23, p<0.005). Corneas treated with topical verteporfin (V) without non-thermal laser or corneas treated with non-thermal laser (NTL) without verteporfin exhibited an enzymatic digestion time similar to untreated corneas (5.95 h±0.33 and 5.71±0.375 hrs, respectively, p>0.005). Interestingly, corneas that were pretreated with verteporfin for 15 minutes followed by non-thermal laser therapy for six sequences (V+NTL6) demonstrate a significantly slower rate of dissolution compared to untreated corneas (19.75±0.95 hrs, p<0.005). Whereas corneas that underwent the same verteporfin pretreatment that was followed by non-thermal laser therapy for only one sequence (V+NTL1) exhibited a digestion time that was similar to that of untreated corneas (5.96±0.39 hours, p>0.005).

V+NTL$_6$ as compared to untreated corneas, suggesting that both of these treatments confer increased stiffness compared to untreated cornea tissue.

Figure 6:
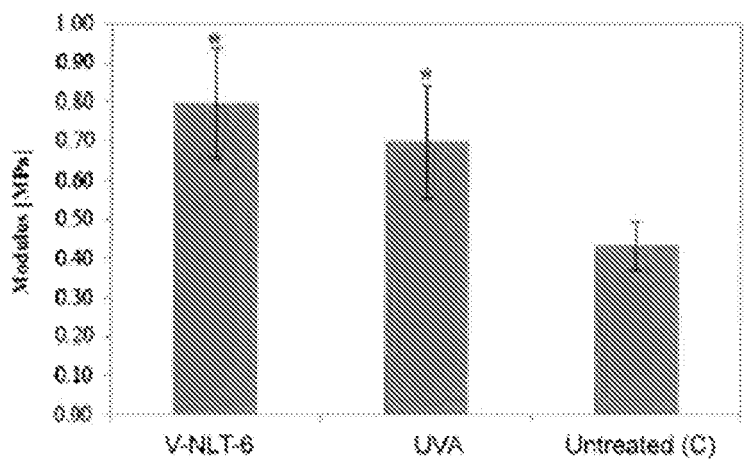
FIG. 6 is a graph demonstrating Young's Modulus for each sample group ((C)=untreated corneas that served as primary controls; (V-NLT-6)=combined treatment of topical verteporfin with non-thermal laser therapy for six treatment sequences; and (UVA)=conventional cross-linking through combined topical riboflavin (0.1% riboflavin/20% dextran)), calculated between 0.08 and 0.10 MPa. Error bars represent ±1 standard deviation. Asterisks (*) represent values that are statistically different from the control group at the 95% confidence level (p<0.05).

Young's modulus was calculated as a linear fit of the final portion of the stress-strain curve, between stress values of 0.08 and 0.10 MPa (FIG. 6). Tissue treated by R+UVA and V+NTL$_6$ had statistically larger moduli than untreated corneas. Corneas treated by V+NTL$_6$ appeared to be slightly more stiff (0.80 vs 0.43 MPa, p<0.005) than those treated by R+UVA (0.70 vs 0.43 MPa, p<0.05), however this difference was not statistically significant.

Example 4. Creep Testing

Figure 7:
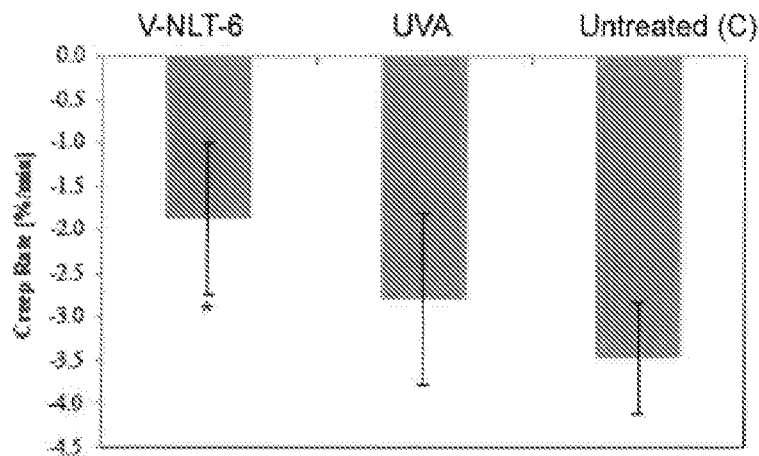
FIG. 7 is a graph demonstrating creep rate for each sample group ((C)=untreated corneas that served as primary controls; (V-NLT-6)=combined treatment of topical verteporfin with non-thermal laser therapy for six treatment sequences; and (UVA)=conventional cross-linking through combined topical riboflavin (0.1% riboflavin/20% dextran)), calculated as the slope of the strain time curve between 0 and 4.25 minutes. Error bars represent ±1 standard deviation. Asterisks (*) represent values that are statistically different from the control group at the 95% confidence level (p<0.05).

Creep testing has been used to evaluate the biomechanical strength of tissue, such as the cornea, by applying a constant stress and monitoring the rate of deformation [21] In this study, cornea tissue was kept under a constant stress using a compression force of 15 N and then the slope of the strain-time curve was calculated between 0 and 4.25 minutes and represented the rate of tissue deformation. Corneas treated by V+NTL6 were found to have a significantly faster creep rate than untreated corneas (−1.87 vs −3.46, p<0.05), indicating that corneas treated by V+NTL6 maintained their initial shape more than untreated corneas. Corneas treated by R+UVA also had a faster creep rate, but the difference was not statistically significant from that of untreated corneas (FIG. 7).

Example 4. Tensile Testing

Using strip-extensometry, stress-strain measurements have demonstrated increased rigidity of the cornea following collagen crosslinking with riboflavin-UVA light[38]. In this study, strip extensometry was performed using rectangular

TABLE 1

| Treatment | Laser Spot Size | Number of Treatment Sequences | Method of Administration | Gross observation | Collagenase time to dissolution (h) |
|---|---|---|---|---|---|
| V-NLT-6 | 7.5 mm | 6 | Topical Verteporfin for 15 min/laser 6 sequences/one drop per sequence. | Cornea rigid | 19.75 ± 0.95 |
| V-NLT-1 | 7.5 mm | 1 | Topical Verteporfin for 15 min/laser for 1 min. | No rigidity | 5.96 ± 0.39 |
| NLT | 7.5 mm | 6 | 6 sequences of laser for 1 min. | No rigidity | 5.71 ± 0.375 |
| V | 7.5 mm | 15 minutes | Topical Verteporfin for 15 min. | No rigidity | 5.95 ± 0.33 |

Biomechanical Testing:

Example 3. Compression Testing

Figure 5:
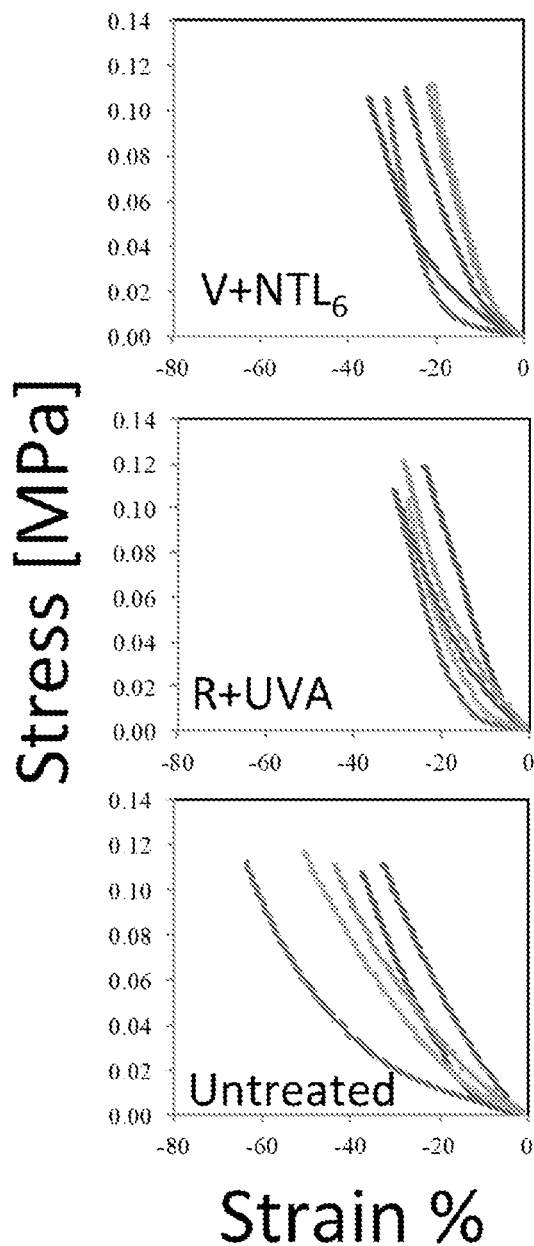
FIG. 5 provides a series of graphs showing the stress-strain data observed for corneas treated with R+UVA and V+VTL-6 as compared to untreated corneas. The data demonstrates that the slope of the stress-strain data is steeper for corneas treated with R+UVA and V+VTL-6 as compared to untreated corneas, suggesting that both treatments confer increased stiffness compared to untreated corneas.

The elasticity of any tissue can be determined by measuring the stress (force on a cross-section point) and its relative strain (proportional deformation)[12,14]. The Young's modulus is the proportion between the stress and strain values and reflects the elasticity of the tissue. A small Young's modulus value reflects more elasticity of a material and is represented in units of Newton/m$^2$. The stress-strain compression data for each treatment group are shown in FIG. 5. Generally, the slope of the stress-strain data is observed to be steeper for corneas treated by R+UVA and strips of corneal tissue that was extracted from untreated and treated corneas. The maximum stress observed prior to failure, the maximum modulus values, and the instantaneous modulus values at specific strain percentages were calculated. The stress-strain data can be broadly separated into two regions: an initial toe region that covers strain values typically observed in vivo, and the region covering extreme deformations not likely to be observed in vivo.

Figure 8:
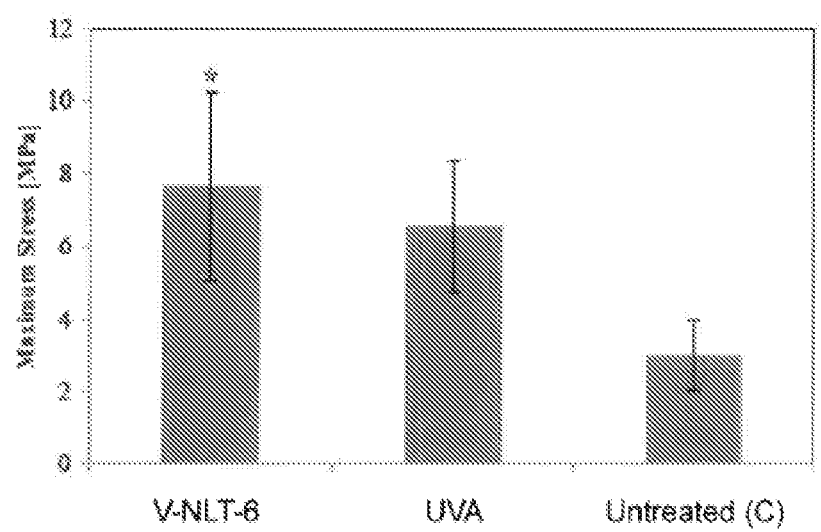
FIG. 8 is a graph demonstrating tensile strength testing for each sample group ((C)=untreated corneas that served as primary controls; (V-NLT-6)=combined treatment of topical verteporfin with non-thermal laser therapy for six treatment sequences; and (UVA)=conventional cross-linking through combined topical riboflavin (0.1% riboflavin/20% dextran)). Maximum modulus measured for all tested samples. Error bars represent ±1 standard deviation. Asterisks (*) represent values that are statistically different from the control group at the 95% confidence level (p<0.05).
Figure 9:
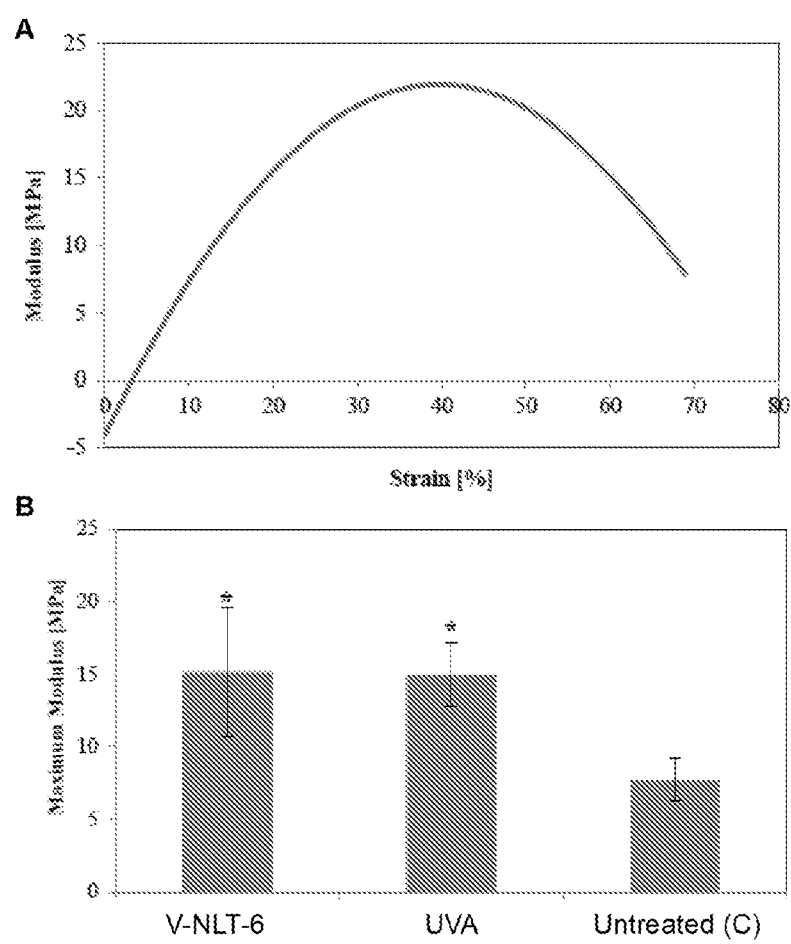
FIGS. 9A-B are a series of graphs demonstrating (9A) representative plot of instantaneous tensile modulus as a function of strain for sample of V+NTL6 group; and (9B) the maximum modulus measured for all tested samples. Error bars represent ±1 standard deviation. Asterisks (*) represent values that are statistically different from the control group at the 95% confidence level (p<0.05).

Specimens treated by R+UVA and V+NTL$_6$ were observed to reach larger stress values prior to failure, relative untreated corneas (FIG. 8). Compared to untreated corneas, the difference was significantly higher for corneas that were treated with V+NTL$_6$ (7.67 vs 3.02 p<0.05). As seen in the compression results, the tested samples showed a nonlinear stress-strain relationship with no clear elastic regime. A representative plot (FIG. 9A) of instantaneous tensile modulus as a function of strain for V+NTL-6 corneas shows that the modulus increased, peaked, and then decreased until the point of sample failure. The maximum modulus value was also calculated and provides a straight-forward method of comparing samples and describing the peak stiffness of the material. We found that corneas treated by R+UVA and V+NTL$_6$ had statistically larger maximum modulus values than untreated corneas (FIG. 9B).

Figure 10:
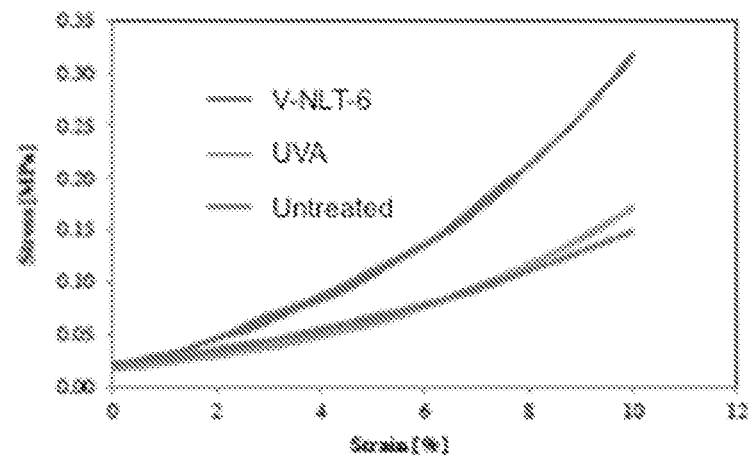
FIG. 10 is a representative plot showing the toe region of the tensile data for one sample from each group tested.
Figure 11:
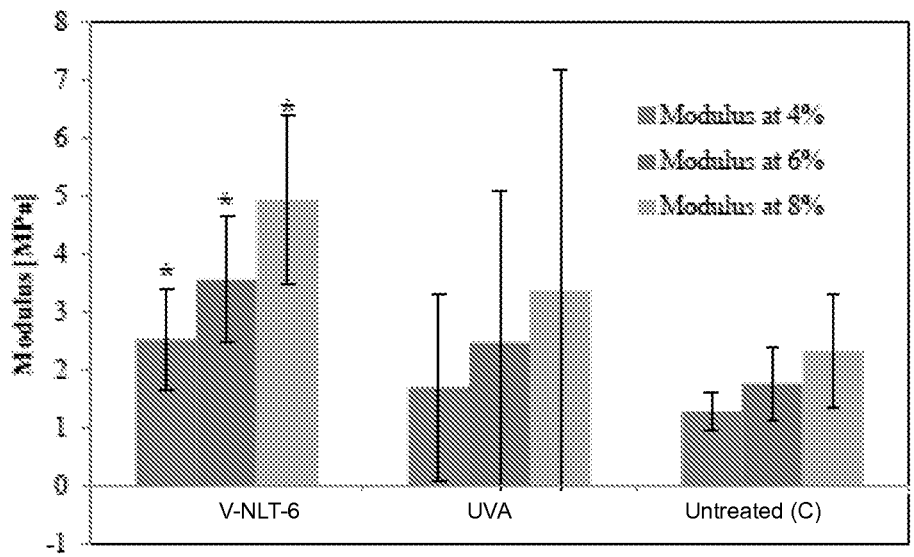
FIG. 11 is a graph demonstrating instantaneous modulus values calculated at 4%, 6%, and 8% strain for all samples tested.

Finally, the initial toe region of each sample group was compared. The stress-strain data was offset such that the sample length at a stress of 0.02 MPa was defined as 0% strain (this offset is equivalent to defining a pre-stress of 0.02 N at the start of the tensile test). A representative plot showing the toe region of the tensile data for one specimen from each sample group is shown in FIG. 10, and the instantaneous modulus values at 4%, 6%, and 8% strain for each sample group are shown in FIG. 11. Corneas treated by V+NTL-6 were found to have statistically larger modulus values than untreated corneas. However, corneas treated by R+UVA were found to have a substantial amount of variability in the toe region, and no statistically significant difference was observed.

Discussion

Intravenous verteporfin and nonthermal laser is typically used to treat diseases of the retina, such as choroidal neovascularization[22,23] in a treatment known as photodynamic therapy (PDT). PDT uses light to activate otherwise inert photosensitizer dyes to produce photochemical reactions through the production of free radical moieties without the generation of heat.[4,5] To our knowledge this is the first paper that investigates the use of topical verteporfin and non-thermal laser (NTL) to induce corneal collagen cross-linking.

Corneas treated with multiple sequences of verteporfin-NLT and corneas treated with riboflavin-UVA demonstrated more resistance to enzymatic degradation and greater biomechanical strength than untreated corneas. These findings suggest that verteporfin-NLT results in strengthening of corneal tissue in a similar manner to that of crosslinking with riboflavin-UVA. For example, when resistance to enzymatic digestion was tested, riboflavin-UVA and six sequences of verteporfin-NLT (V+NTL$_6$) demonstrated increased resistance with longer dissolution times (20.06±1.23 hours and 19.75±0.95 hours, respectively, p<0.005) compared to untreated corneas (5.47±0.2 hours). Interestingly, corneas treated with only one sequence of verteporfin-NLT, corneas treated with only topical verteporfin without PDT, or corneas treated with PDT without verteporfin demonstrated similar dissolution times as untreated corneas.

These results indicate that verteporfin-PDT induces cross-linking of collagen within the cornea. Similar observations have been made when verteporfin-PDT was used to treat other tissues comprised of collagen.[24,25] At cellular level, it has been suggested that photodynamic therapy generated singlet oxygen interacts with photo-oxidizable amino acid residues in one protein molecule to generate reactive species, which in turn interact non-photochemically with residues of free amino groups in another protein molecule to form a crosslink. In some cases, photochemically generated free radicals may be involved in crosslinking. In vascular researches it has been found that, photodynamic laser therapy induced collagen matrix changes, including crosslinking, which resulted in increased resistance to protease digestion in vascular tissue.[24,4] This effect appears to be principally mediated by free radical interactions with amino acids, which lead to conformational and other chemical changes that modify biologically active or specific binding sites of these proteins. It is known that collagen type is the major type of collagen in human corneal stroma.[26] Vascular studies also identified that photodynamic laser therapy of collagen type I, generated high molecular weight complexes, suggesting cross-linking with increased thermal and mechanical stability.[24,25] Distinct collagen-to-collagen crosslinks have been reported after photodynamic laser therapy of matrix gel solution containing collagen alone.[4,24,25]

Verteporfin-photodynamic laser therapy has been reported to be an effective treatment for cornea neovascularization, which can cause leakage of fluid, lipid deposits, and cornea scarring.[6,7,8,27,28] In these cases, neovascular corneas were treated with one sequence of PDT for 15 minutes after intravenous verteporfin administration. There are several important differences between the prior studies that used photodynamic therapy to treat cornea neovascularization and this study. Here, verteporfin was applied topically onto a de-epithelialized cornea, while it was applied intravenously in the previous studies. In this study, the cornea epithelium was removed to increase penetration of riboflavin into the cornea stroma. Finally, for the studies described above six sequences of verteporfin-PDT treatments were applied since. Corneas treated with six sequences of verteporfin-PDT sequences demonstrated results similar to that of riboflavin-UVA.

One advantage of verteporfin-PDT is that the laser can be focused to treat specific areas and depths of the cornea. This will allow the treatment of thin corneas and represents a major advantage over UVA CXL, which typically is not used to treat corneas thinner than 400 μm due to concern of damaging the cornea endothelium.[36,31] Verteporfin-PDT may also be used to treat ectatic corneas that are thinner than 400 μm and includes keratoconus, pellucid marginal degeneration, or post-LASIK ectasia. UVA-CXL of the residual bed in ectatic disorders like post-LASIK ectasia[32] might result in significant corneal endothelial cell damage and potentially damage the lens epithelium when residual bed thickness becomes less than 250 μm.[33] By comparison, V-NLT CXL would be limited to the two-photon volume of the focusing lens, which can be precisely controlled by moving the lens respective to the cornea. The entire residual bed could undergo collagen cross-linking without exposing the corneal endothelium to the damaging effects of free radicals. Another advantage of V-NLT CXL that it can be performed regionally and is not limited solely to the anterior cornea, the effects of different treatment strategies involving different depths, thicknesses, and patterns which could be easily tested and may provide improved treatment outcomes. V-NLT CXL can be performed regionally to stop corneal ectasia exacerbated by radial keratotomy, which have been managed by UVA CXL with unpredictable results.[34] Regional V-NLT CXL may also be applied as a refractive enhancement of a regressed previous astigmatic keratotomy that has recently been reported with UVA CXL.[35] Moreover, V-NLT CXL could be used to reshape the cornea, by compacting the tissue in certain areas thus acting as a refractive tool. It is also possible that V-NLT CXL could be used to hold the shape of the cornea after the use of orthokeratology contact lenses, which normally only has a temporary effect on the shape and refraction of the cornea In this study we report for the first time that verteporfin non-thermal photodynamic laser increases corneal mechanical stiffness and resistance to enzymatic collagenase degradation. These results suggest that verteporfin non-thermal photodynamic laser induces crosslinking cornea tissue that is similar to that of collagen crosslinking (CXL) using ultraviolet-A (UVA) irradiation combined with riboflavin.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

REFERENCES

1. Spoerl E, Huhle M, Kasper M, Seiler T. Erhɛ̌ohung der Festigkeit der Hornhaut durch Vernetzung [Artificial stiffening of the cornea by induction of intrastromal crosslinks]. Ophthalmologe 1997; 94:902-906
2. Wollensak G, Spoerl E, Seiler T. Stress-strain measurements of human and porcine corneas after riboflavin-ultraviolet-A-induced cross-linking. J Cataract Refract Surg 2003; 29:1780-1785
3. Therapy (TAP) Study Group. Photodynamic therapy of subfoveal choroidal neovascularization in age-related macular degeneration with verteporfin: Two-year results of 2 randomized clinical trials—TAP Report 2. Arch Ophthalmol 2001; 119:198-207.
4. Jenkins M P, Buonaccorsi G, MacRobert A, Bishop C C, Bown S G, McEwan J R. Intra-arterial photodynamic therapy using 5-ALA in a swine model. Eur J Vasc Endovasc Surg. 1998; 16:284-291.
5. LaMuraglia G M, ChandraSekar N R, Flotte T J, Abbott W M, Michaud N, Hasan T. Photodynamic therapy inhibition of experimental intimal hyperplasia: acute and chronic effects. J Vasc Surg. 1994; 19:321-331.
6. Brooks B J, Ambati B K, Marcus D M, Ratanasit A. Photodynamic therapy for corneal neovascularization and lipid degeneration. Br J Ophthalmol. 2004; 88:840.
7. Yoon K C, Ahn K Y, Lee S E, Kim K K, Im S K, Oh H J, et al. Experimental inhibition of corneal neovascularization by photodynamic therapy with verteporfin. Curr Eye Res. 2006; 31:215-24.
8. Fossarello M, Peiretti E, Zucca I, Serra A. Photodynamic therapy of corneal neovascularization with verteporfin. Cornea. 2003; 22:485-8.
9. Wollensak G, Redl B. Gel electrophoretic analysis of corneal collagen after photodynamic cross-linking treatment. Cornea 2008; 27:353-356.
10. Spoerl E, Wollensak G, Seiler T. Increased resistance of crosslinked cornea against enzymatic digestion. Curr Eye Res. 2004; 29(1):35-40.
11. Charulatha V, Rajaram A. Crosslinking density and resorption of dimethyl suberimidate-treated collagen. J Biomed Mater Res. 1997; 36: 478-486.
12. Wollensak G, Spoerl E, Seiler T. Stress-strain measurements of Human and porcine corneas after riboflavin-ultraviolet-A-induced cross-linking. J Cataract Refract Surg 2003; 29:1780-1785
13. Kohlhaas M, Spoerl E, Schilde T, Unger G, Wittig C, Pillunat L E. Biomechanical evidence of the distribution of cross-links in corneas treated with riboflavin and ultraviolet A light. J Cataract Refract Surg 2006; 32:279-283
14. Lanchares E, Del Buey M A, Cristobal J A, Lavilla L, Calvo B. Biomechanical property analysis after corneal collagen cross-linking in relation to ultraviolet A irradiation time. Graefes Arch Clin Exp Ophthalmol 2011; 249:1223-1227
15. Wollensak G, Iomdina E. Long-term biomechanical properties of rabbit cornea after photodynamic collagen crosslinking. Acta Ophthalmol 2009; 87:48-51. Available at: http://onlinelibrary.wiley.com/doi/10.1111/j.1755-3768.2008.01190.x/pdf. Accessed Dec. 4, 2012.
16. Wollensak G, Iomdina E. Biomechanical and histological changes after corneal crosslinking with and without epithelial debridement. J Cataract Refract Surg 2009; 35:540-546.
17. Wollensak G, Wilsch M, Spoerl E, Seiler T. Collagen fiber diameter in the rabbit cornea after collagen crosslinking by riboflavin/UVA. Cornea 2004; 23:503-507
18. Wollensak G, Redl B. Gel electrophoretic analysis of corneal collagen after photodynamic cross-linking treatment. Cornea 2008; 27:353-356.
19. Tanaka S, Avigad G, Brodsky B, Eikenberry E F. Glycation induces expansion of the molecular packing of collagen. J Mol Biol 1988; 203:495-505
20. Kohlhaas M, Spoerl E, Schilde T, Unger G, Wittig C, Pillunat L E. Biomechanical evidence of the distribution of cross-links in corneas treated with riboflavin and ultraviolet A light. J Cataract Refract Surg 2006; 32:279-283.
21. Ahmed Elsheikht and Kevin Anderson. Comparative study of corneal strip extensometry and inflation tests. J R Soc Interface. 2005 Jun. 22; 2(3): 177-185.
22. Treatment of Age-Related Macular Degeneration With Photodynamic Therapy (TAP) Study Group. Photodynamic therapy of subfoveal choroidal neovascularization in age-related macular degeneration with verteporfin: one-year results of 2 randomized clinical trials—TAP Report 1. Arch Ophthalmol 1999; 117:1329-1345.
23. Therapy (TAP) Study Group. Photodynamic therapy of subfoveal choroidal neovascularization in age-related macular degeneration with verteporfin: Two-year results of 2 randomized clinical trials—TAP Report 2. Arch Ophthalmol 2001; 119:198-207.
24. Marcus Overhaus, et al. Photodynamic Therapy Generates a Matrix Barrier to Invasive Vascular Cell Migration. (Circ Res. 2000; 86:334-340.)
25. Shen H-R, Spikes J D, Kopecekoya´ P, Kopecek J. Photodynamic crosslinking of proteins, I: model studies using histidine- and lysinecontaining N-(2-hydroxypropyl) methacrylamide copolymers. J Photochem Photobiol. 1996; 34:203-210.
26. Nakayasu K, Tanaka M, Konomi H, Hayashi T. Distribution of types I, II, III, IV and V collagen in normal and keratoconus corneas. Ophthalmic Res. 1986; 18(1):1-10
27. Al-Abdullah A A, Al-Assiri A. Resolution of bilateral corneal neovascularization and lipid keratopathy after photodynamic therapy with yerteporfin. Optometry. 2011 April; 82 (4):212-4. Epub 2011 Jan. 8.
28. Al-Torbak A A. Photodynamic therapy with yerteporfin for corneal neovascularization. Middle East Afr J Ophthalmol. 2012 April-June; 19(2):185-9.
29. Tsutomu Igarashi, Chiemi Yaguchi, Michinori Inage, Hisaharu Suzuki, Hiroshi Takahashi. Topographical alteration in the cornea after photodynamic therapy for neovascularization in lipid keratopathy. Journal of Refractive Surgery•Vol. 28, No. 11, 2012 775
30. H. U. Celik et al., "Accelerated corneal crosslinking concurrent with laser in situ keratomileusis," J. Cataract Refract. Surg. 38(8), 1424-1431 (2012).

31. G. D. Kymionis et al., "Corneal collagen cross-linking with riboflavin and ultraviolet-A irradiation in patients with thin corneas," Am. J. Ophthalmol. 153(1), 24-28 (2012).
32. P. I. Condon, M. O'Keefe, and P. S. Binder, "Long-term results of laser in situ keratomileusis for high myopia: risk for ectasia," J. Cataract Refract. Surg. 33(4), 583-590 (2007).
33. H. U. Celik et al., "Accelerated corneal crosslinking concurrent with laser in situ keratomileusis," J. Cataract Refract. Surg. 38(8), 1424-1431 (2012).
34. Mazzotta C, Baiocchi S, Denaro R, Tosi G M, Caporossi T. Cornea. 2011 February; 30(2):225-8. Corneal collagen cross-linking to stop corneal ectasia exacerbated by radial keratotomy.
35. Kanellopoulos A J. Very high fluence collagen cross-linking as a refractive enhancement of a regressed previous astigmatic keratotomy. J Refract Surg. 2013 July; 29(7):504-5.
36. F. Raiskup-Wolf et al., "Collagen crosslinking with riboflavin and ultraviolet-A light in keratoconus: long-term results," J. Cataract Refract. Surg. 34(5), 796-801 (2008).
37. D. Chai et al., "Quantitative assessment of UVA-riboflavin corneal cross-linking using nonlinear optical microscopy," Invest. Ophthalmol. Visual Sci. 52(7), 4231-4238 (2011).
38. F. Hafezi et al., "Collagen crosslinking with ultraviolet-A and hypoosmolar riboflavin solution in thin corneas," J. Cataract Refract. Surg. 35(4), 621-624 (2009).
40. Photodynamic Therapy Generates a Matrix Barrier to Invasive Vascular Cell Migration. Marcus Overhaus, Joerg Heckenkamp, Sylyie Kossodo, Dariusz Leszczynski, Glenn M. LaMuraglia. (Circ Res. 2000; 86:334-340.)

What is claimed is:

1. A method for increasing corneal rigidity in a subject, comprising:
    identifying a subject who has keratoconus, pellucid marginal degeneration, post-operative ectasia or who has refractive defects and plans to undergo a refractive surgical procedure at a later time;
    topically administering an effective amount of a composition comprising verteporfin to the cornea of the subject; and
    irradiating the cornea with non-thermal laser light with a wavelength of 687 nm to 693 nm, wherein the administering and irradiating steps are repeated for a total of at least six times,
    wherein the irradiating step comprises continuous exposure to non-thermal laser light for 30 to 60 seconds in duration, and targeting the non-thermal laser light to a depth within the cornea in a range of 50 microns to 500 microns.

2. The method of claim 1, wherein the refractive surgical procedure is radial keratotomy (RK), photorefractive keratectomy (PRK), or laser in-situ keratomileusis (LASIK).

3. The method of claim 1, wherein the verteporfin composition is a lotion, gel, cream, ointment, solution, spray, paste or aerosol composition.

4. The method of claim 1, wherein topically administering a composition comprising verteporfin comprises applying eye drops comprising a verteporfin solution to the surface of the cornea.

5. The method of claim 1, further comprising determining the amount of collagen cross-linking in the cornea.

6. The method of claim 1, wherein the verteporfin composition comprises 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, or 10.0 mg/ml of verteporfin.

7. The method of claim 1, wherein the composition comprising verteporfin is administered to the cornea one to twenty minutes, one to ten minutes, ten to twenty minutes, two to nine minutes, three to seven minutes, four to six minutes, or four to five minutes prior to irradiating the cornea with a non-thermal laser.

8. The method of claim 1, wherein the non-thermal laser light has an intensity in a range of 200 mW/cm$^2$ to 650 mW/cm$^2$, or in a range of 575 mW/cm$^2$ to 625 mW/cm$^2$.

9. The method of claim 1, wherein the irradiating step comprises targeting the non-thermal laser light to a depth within the cornea in a range of 100 microns to 450 microns, 150 microns to 400 microns, 200 microns to 350 microns, 250 microns to 300 microns, 50 microns to 250 microns, or 250 microns to 500 microns.

10. A method for increasing corneal rigidity in a subject, comprising:
    (a) identifying or having identified a subject who has keratoconus, pellucid marginal degeneration, post-operative ectasia or who has refractive defects and plans to undergo a refractive surgical procedure at a later time;
    (b) topically administering an effective amount of a composition comprising verteporfin to the cornea of the subject for 15 minutes;
    (c) irradiating the cornea with non-thermal laser light with a wavelength of 687 nm to 693 nm for 60 seconds;
    wherein step (c) is repeated for a total of six times, and wherein an effective amount of the composition comprising verteporfin is administered to the cornea before each time step (c) is repeated.

* * * * *